US005643533A

United States Patent [19]
Fishman

[11] Patent Number: 5,643,533
[45] Date of Patent: Jul. 1, 1997

[54] METHOD OF PACKAGED GOODS STERILIZATION

[76] Inventor: Yoram Fishman, 2375 Third St., Riverside, Calif. 92507

[21] Appl. No.: 439,764

[22] Filed: May 12, 1995

[51] Int. Cl.$^6$ .................................................. A61N 2/00
[52] U.S. Cl. .................. 422/1; 422/38; 435/34; 435/39; 426/521
[58] Field of Search ................... 422/1, 25, 26, 422/38; 435/34, 38, 39; 436/1; 53/425; 426/401, 521

[56] References Cited

U.S. PATENT DOCUMENTS

| | | | |
|---|---|---|---|
| 3,454,406 | 7/1969 | Alderton | 422/1 |
| 3,618,283 | 11/1971 | Moore et al. | 422/28 |
| 3,754,368 | 8/1973 | Moore et al. | 422/25 |
| 3,857,677 | 12/1974 | Moore et al. | 422/37 |
| 4,057,391 | 11/1977 | Yasmaguchi | 422/25 |
| 4,459,936 | 7/1984 | Karle | 422/26 |
| 4,467,588 | 8/1984 | Carveth | 53/425 |
| 4,639,421 | 1/1987 | Sage, Jr. | 435/25 |
| 4,718,463 | 1/1988 | Jurgens, Jr. et al. | 422/25 |
| 4,847,066 | 7/1989 | Honigs et al. | 436/1 |
| 4,896,768 | 1/1990 | Anderson | 206/210 |
| 4,947,620 | 8/1990 | Carter | 53/425 |
| 4,997,083 | 3/1991 | Loretti et al. | 206/219 |
| 4,998,400 | 3/1991 | Suzuki et al. | 53/425 |
| 5,345,574 | 9/1994 | Franchi | 53/431 |

OTHER PUBLICATIONS

Block, *Distinfection, Sterilization, & Preservation*, 1991, pp. 514–515 & 1047–1049.

*Primary Examiner*—Christopher Kim
*Attorney, Agent, or Firm*—Alan S. Raynes

[57] ABSTRACT

Methods for heat treating goods to remove or prevent contaminants include the steps of identifying the contaminant or contaminants present and then heat treating the goods at a temperature in the range of 117°–150° F. Such heat treatment can be carried out on prepackaged, bulk quantities of contaminated or non-contaminated goods.

20 Claims, No Drawings

METHOD OF PACKAGED GOODS STERILIZATION

BACKGROUND OF THE INVENTION

1. Field of the Invention

This invention relates to methods for sterilizing packaged goods and in particular towards relatively low temperature sterilization methods for packaged goods.

2. The Related Art

Sterilization of packaged goods is necessary to destroy harmful bacteria or other organisms living inside of the package. There are numerous methods used to sterilize packages and/or the contents of a package, including steam sterilization, gas sterilization, and irradiation. Other techniques include exposing the packaged goods to heat in the presence of water, and exposing the packaged goods to heat in the presence of an anti-bacterial agent within the container.

Steam sterilization is typically carried out in an autoclave, a tower autoclave, or a rotomat and employs saturated steam under pressure. The autoclave is commonly operated at a temperature of about 120° C. Due to this relatively high temperature, many types of articles cannot be treated in such a manner. For other articles, the desired packaging cannot survive such conditions. As a result, such articles may be steam sterilized and then packaged.

Gas sterilization is commonly carried out using gases such as ethylene oxide or propylene oxide. A variety of gas sterilization processes have been carried out, for example, using the steps of pre-humidification, heating and evacuation of a chamber, and exposure to a high concentrations of gas for a period of up to 20 hours. Gas sterilization may lead to the formation of undesirable components such as glycol in the presence of water.

Irradiation has also proven effective in sterilizing packaged goods, including the use of gamma radiation at levels of about 0.05 to 2.0 megarads (mR). However, a drawback to the irradiation method is the high cost of the procedure. Such high cost is dictated by factors including the equipment used and the numerous regulations which must be followed to insure safety. Due to the costs involved, there are relatively few irradiation facilities for performing sterilization, and therefore the time necessary to ship goods, have them irradiated, then shipped back to a manufacturer can be extensive.

U.S. Pat. No. 3,618,283 to Moore et al. discloses a method for sterile packaging of articles such as catheters, hypodermic needles, sutures, etc., in a flexible container. The method requires the presence of a liquid anti-bacterial agent which contacts the exposed surfaces of the container and the contents of the container. The container must be flexible so that it can be kneaded, rolled, or otherwise worked in order to completely contact all interior surfaces of the container and all exposed surfaces of the articles with the anti-bacterial solution. After all surfaces have been contacted, the container is heated. The anti-bacterial agents which may be used include a soap solution with 1 to 2% hexachlorophene, a solution of an iodophor, a 3% solution of parachloromethahexanol, a 1 to 5% solution of Merthiolate, and an aqueous 3% solution of Zephiran.

U.S. Pat. No. 3,754,368 to Moore et al. discloses a method of sterile packaging including sealing a product comprising a liquid, which is at least predominantly water, in a container capable of withstanding a temperature of 212° F. at atmospheric pressure. Next the container and its contents are heated for at least 24 hours and up to 200 or more hours, at a temperature above 170° F. and below 212° F. and below the boiling temperature of the liquid.

Depending on the goods to be sterilized, and the packaging desired to be used, the temperature at which sterilization is carried out can be a critical feature of the sterilization process. For example, certain cosmetics are made from emulsions or solutions which will separate at temperatures such as those noted above. Other items will melt or be otherwise chemically altered at such temperatures. For example, certain packaging such as shrink-wrap or other polymer packaging often have a relatively low melting point.

It would be desirable to have a relatively low temperature method for sterilization of a wide range of articles and packages, without the need for exposure to anti-bacterial agents. It would also be desirable for the sterilization method to be inexpensive, and safe from dangers such as those which could occur during the radiation process. Embodiments of the present invention are directed towards these and other objectives.

SUMMARY OF THE DISCLOSURE

Embodiments of the present invention relate to a method for sterilizing packaged goods the method including the step of heating the packaged goods to a temperature in the range of approximately 117°–150° F. for a time sufficient to sterilize the packaged goods. In another aspect of embodiments of the present invention, the heating step may be carried out at a temperature in the range of 122°–140° F.

In another aspect of certain embodiments, the packaged goods may be heated for a time in the range of 12 hours to 14 days in order to sterilize the packaged goods.

Embodiments of the present invention also include a method for sterilizing a packaged product contaminated with one or more organisms of the genera pseudomonas, escherichia, serratia, klebsiella, proteus, enterobacter, actinetobacter, streptococcus, staphylococcus, aspergillus and candida albicans, the method including the step of heating the packaged product to a temperature in the range of 117°–150° F. for a time sufficient to lower the number of contaminant organisms to less than 10 contaminant organisms per gram of product.

Still other embodiments of the present invention include a method for treating bulk quantities of goods contaminated with a microorganism, the method comprising the steps of: (a) determining the quantity of contaminant microorganisms in a sample taken from the bulk quantity of goods; (b) determining whether the microorganisms are a microorganism selected from the group consisting of a bacteria, a yeast, or a mold; (c) determining a temperature at which the microorganisms can be destroyed within the range of approximately 122°–140° F.; (d) heating bulk quantities of the goods at a temperature in the range of 122°–140° F. for a time period in the range of 12 hours to 14 days; and (e) measuring the contaminants remaining in a unit quantity of the goods after heating.

DETAILED DESCRIPTION OF PREFERRED EMBODIMENTS

This description contains the best mode for carrying out the present invention and is made for the purpose of illustrating the principles of the invention, and is not to be taken in a limiting sense. The scope of the invention is determined by reference to the appended claims.

Embodiments of the present invention relate to a process for sterilizing packaged goods using relatively low temperatures, without the necessity of using an anti-bacterial agent or exposing the packaged goods to radiation.

A first step in embodiments of the invention is to determine whether any bacterial or other organisms are present in the goods. Three tests may be performed for such a determination, including (1) total bacterial count; (2) yeast and mold count; and (3) gram negative bacteria screen test.

To perform the above-mentioned tests, the following steps may be undertaken. First, 10 ml or 10 grams of the product to be tested for contamination is placed into 90 ml of a sterile letheen broth and shaken well to distribute the product in the solution. The media is sterilized in a Market forge-sterilmatic autoclave at 15 lb/in$^2$ at 121° C. for 15 minutes.

For the total bacterial count test, the procedure is as follows: (1) transfer 1 ml of the mixed solution to a sterile petri dish; (2) add sterile liquefied trypticase soy agar to the petri dish, swirl and allow to solidify; (3) incubate the plate at 35° C. for 48 hours (using, for example, a Fisher Scientific—Isotemp Incubator Model 655D); (4) count and average the bacterial presence, multiply by the appropriate dilution factor and report the results as plate count per gram or ml.

For the yeast and mold count test, the procedure is as follows: (1) transfer 1 ml of the mixed solution into a sterile petri dish; (2) add sterile liquefied Sabourand dextrose agar, swirl, and allow to solidify; (3) incubate the dish at room temperature for five to seven days; and (4) average the count obtained and report yeast or mold per milliliter of sample.

For the gram negative bacteria screen test, the procedure is as follows: (1) incubate the broth solution at 35° C. for 24 hours; (2) streak a sample of the broth solution on MacConkey Agar; (3) incubate the plate at 35° C. for 24–48 hours; and (4) report the results as either positive or negative for gram negative bacteria.

From the results of the above tests the presence of contaminants and certain information regarding their structure may be determined. More detailed information may be obtained by performing a gram stain test. Then, the species of bacteria may be further identified by using a bacterial identification kit such as an API 20E enterobacteriaceae system. Yeast and mold identification testing can also be carried out using, for example, a microscopic wet mount test and an API 20C clinical yeast system.

Applicant has found that a variety of microorganisms can be destroyed at relatively low temperatures, including temperatures within the range of 117°–150° F. In general terms, higher temperatures will destroy contaminants faster than lower temperatures. However, certain chemical formulations for goods and/or packaging materials cannot survive higher temperatures because at such temperatures they will separate, melt, and/or break down. Therefore, more preferred embodiments of the present invention include methods having an application of heat in the range of 122°–140° F.

One method to determine whether contaminant microorganisms can be destroyed at a temperature within the more preferred range is to place the contaminants into an oven, (such as a Fisher-Isotemp 500 Series) heat the oven to a temperature within the range of 122°–140° F. for a variety of times ranging from 12 hours to 14 days and then determine if any microorganisms are viable after such time period.

Various kinds of gram-negative and gram positive bacteria, yeast and fungi have been isolated from cosmetic products. Some of the various genera which have been isolated and which can be treated include pseudomonas, escherichia, serratia, klebsiella, proteus, enterobacter, actinetobacter, streptococcus, staphylococcus, aspergillus and candida albicans.

In one example, seven different bacterial strains were tested to determine whether low temperature treatment could destroy them. These strains included those set forth in Table 1. Three tubes containing 100 ml each of sterile tryptic soy broth were inoculated with 0.1 ml of bacterial suspension per strain, for a total of 21 tubes. Next the tubes were incubated at 37° C. for 24 hours.

Good growth of bacterial was observed in each tube. The number of viable organisms per strain was recorded on one set of seven tubes. A second set of seven tubes was kept at room temperature. The third set of seven tubes was put into a treatment chamber at a temperature within the range of 122°–140° F. for 24 hours. After treatment, 0.05 ml was inoculated from each strain and the control tubes onto trypticase soy agar plates. The plates were incubated for 48 hours, and the number of organisms on the plates was then quantified. The results, as shown in Table 1 (measured in organisms per milliliter), indicated that all seven organisms were sufficiently destroyed so that large scale treatment could be carried out and any contamination from one or more of the seven organisms would be sufficiently eliminated.

TABLE 1

Comparison of contaminants remaining in untreated, control and heat treated specimens.

| ORGANISM | UNTREATED | CONTROL | TREATED |
|---|---|---|---|
| 1. escherichia coli | >10$^6$ org/ml | >10$^6$ org/ml | <10 org/ml |
| 2. pseudomonas aeruginos | >10$^6$ org/ml | >10$^6$ org/ml | <10 org/ml |
| 3. klebsiella oxytoca | >10$^6$ org/ml | >10$^6$ org/ml | <10 org/ml |
| 4. staphylococcus aureus | >10$^6$ org/ml | >10$^6$ org/ml | <10 org/ml |
| 5. streptococcus species | >10$^6$ org/ml | >10$^6$ org/ml | <10 org/ml |
| 6. candida albicans | >10$^6$ org/ml | >10$^6$ org/ml | <10 org/ml |
| 7. enterobacter aerogenes | >10$^6$ org/ml | >10$^6$ org/ml | <10 org/ml |

From the above remits it was determined that the packaged goods can be dry heat treated at relatively low temperatures in order to destroy the seven contaminants specified above. For cosmetics after treatment, a measurement of less than 10 organisms per milliliter (or 10 organisms per gram) is generally sufficient for effective sterilization purposes. It is believed that the elevated temperatures result in the oxidation of the contaminant microorganisms.

Embodiments of the present invention also contemplate large scale heat treatment of packaged goods. Applicants have fabricated a dry heat chamber designed to sterilize bulk quantities of packaged goods at the same time. The chamber measures approximately 8×9×24 feet. It may be constructed from an aluminum outer casing, insulated with polyethylene foam. The inner walls of the chamber may be reinforced with wood and metal. The chamber consists of two side doors with a double back door in the rear for forklift access. The doors have a thick rubber lining to prevent heat loss.

The chamber is gas heated, and has a tunnel measuring 8.5 inches by 3 feet by twenty feet long, the tunnel containing multiple vents for distributing the heat. The tunnel is disposed along the roof of the chamber. The heating is powered by Dayton unit heater aerotherms having blower-thermal input capacity of 200,000 BTU/hr and thermal output capacity of 160,000 BTU, and a three horsepower electric motor for distributing the heat. A Honeywell controller and gauge having a range of 55°–170° F. is used to set the temperature. The temperature within the chamber is monitored by temperature gauges mounted in the front and rear of the chamber. The atmosphere in the chamber may be air. No particular humidity control is necessary. The design of the chamber need not be limited to the exact specifications above.

Various experimental runs in the chamber with bulk quantities of contaminated samples have been carried out. These tests were performed for varying times at varying temperatures in air. It is believed that the relative important to the air is not important to the operation of the method.

In one test, contaminated shampoo was treated. The contaminant was determined to be pseudomonas species. It was determined that heat treatment for 48 hours at 137° F. would be sufficient to sterilize the shampoo. The shampoo bottles were packaged in high density polyethylene (HDPE) bottles and placed into 24 pack shipping containers. Over 23,000 bottles were heat treated at 137° F. for 48 hours. Prior to the treatment, the contamination was measured at greater than $10^6$ organisms per gram. After treatment, the total bacterial count was less than 10 organisms per gram. The post-treatment testing was carried out using an A.Q.L. sampling plan based on Mil. Std. 105D. Neither the packaging nor the shampoo was adversely affected by the heat treatment.

Another test run was carried out for a cosmetic moisture lotion packaged into frosted glass bottles decorated with gold hot stamp logo and color silkscreen, covered with silver lined caps. The bottles were placed into unit cartons with inner inserts and sealed into six packs with clear polyvinyl chloride (PVC) film, and the six packs placed into 8 pack master shipping containers. During the same test run, an eye cosmetic was also treated. The eye cosmetic was packaged into frosted glass jars with silver hot stamp logo, sealer discs, and covered with silver lined caps. The filled jars were placed into unit cartons with inner inserts and put into three pack containers. Six three pack containers were then placed into tamper resistant master shipping containers.

Both the moisture lotion and eye cosmetic were found to be contaminated with a gram positive cocci bacteria. Over 140,000 bottles and jars were heat treated at 131° F. for seven days. Prior to heat treatment, the total bacterial count was greater than $10^5$ organisms per gram. After treatment the total bacterial count was less than 10 organisms per gram. The post-treatment testing was carried out using an A.Q.L. sampling plan based on Mil. Std. 105D. Neither the products nor the packaging were adversely affected by the heat treatment.

In another test run, an eye cream was packaged into round glass jars with silver hot stamp logo, sealer discs, and covered with silver lined caps. Some of the filled jars were placed into unit cartons with inner inserts and put into three packer containers with six three packer containers put into tamper resistant master shipper containers. Other filled jars were packaged 24 jars into tamper resistant master shipper containers. The eye cream was found to be contaminated with a gram positive bacteria. The packaged jars were heat treated at 131° F. for 8 days. Prior to heat treatment the total bacterial count was greater than $10^4$ organisms per gram. After treatment the total bacterial count was less than 10 organisms per gram. The post-treatment testing was carded out using an A.Q.L. sampling plan based on Mil. Std. 105D. Neither the eye cream nor the packaging was adversely affected by the heat treatment.

Another test was performed on a bulk quantity of cosmetic product which was not in its final packaged state, but was contained in a stainless steel tote holding over 1700 kilograms of the cosmetic product. The product was found to contain a gram positive bacteria. The product was heat treated at 140° F. for 14 days. Prior to the heat treatment the contamination was measured as a total bacterial count of greater than $6.1 \times 10^3$ organisms per gram. After the treatment, the total bacterial count was less than 10 organisms per gram. The post-treatment testing was carried out using an A.Q.L. sampling plan based on Mil. Std. 105D. The product was not adversely affected by the treatment.

As can be seen by the above examples, the method of the present invention is applicable to a variety of products being treated at a variety of times and temperatures. Applicant has found a relationship exists between the treatment time and temperature. For example, a contaminant may be destroyed at a temperature of 122° F. if held there for 7 days. The same contaminant may be destroyed at a temperature of 130° F. if held there for 2 days. The temperature at which a particular product should be treated may be dependent on a variety of factors such as the chemical makeup of the product or the packaging used with the product. Applicant has found that numerous contaminants can be effectively destroyed within the preferred range of 122° F. to 140° F.

Additionally, certain embodiments of the invention can be carried out without specific identification of the contaminant. For example, different bacteria having similar structural characteristics may act in similar ways in response to the application of low level heat, so that specific identification of the bacteria is not always necessary to successfully carry out the method.

In another aspect of embodiments of the invention, once a particular contaminant has been identified in a product and the appropriate time and temperature for treatment is determined, this information can be useful in determining the appropriate temperature for treating the same or a similar contaminant in another product. Thus, the preliminary steps, such as the determination of whether the contaminant can be destroyed at a temperature in the range of 117°–150° F., or the more preferred range of 122°–140° F., may not be necessary for future treatment of a product once its contaminant has already been treated in a prior run. However, different products having the same contaminant will sometimes have to be treated at different temperatures and times because the products themselves have different maximum temperatures they can survive without breaking down or separating. For example, cosmetic creams may have a lower breakdown temperature than shampoos, so the same contaminant in both may be treated at different temperatures and for different times.

Embodiments of the present invention allow for relatively low temperature treatment of contaminated good after the goods have been packaged. By using a large treatment chamber, bulk quantities of goods can be treated together. Furthermore, processes according to embodiments of the present invention do not require the presence of an antibacterial agent, and do not utilize a dangerous technology.

In another aspect of embodiments of the invention, packaged goods may be heat treated regardless of whether it has been determined that the goods are contaminated. This is because it may be more efficient for a manufacturer to treat all packaged goods coming off the line to insure there is no contamination. Treatment according to embodiments of the present invention does not require a large number of complex or dangerous steps, and can be carried out at relatively low cost. Thus, packaged goods may be heat treated in the range of 117°–150° F., or the more preferred range of 122°–140° F., depending on the goods and packaging, without first determining whether they contain any contaminants, in order to insure that the goods are sufficiently sterile for consumer use.

The scope of the present invention is not limited to the specific embodiments discussed above. As noted above, variations in the time and temperature of treatment may be used, depending on the product and its packaging. Furthermore, methods other than those described above may be used for determining the presence of contaminants and for identifying the specific contaminant or contaminants present.

What is claimed is:

1. A method for sterilizing goods comprising the steps of providing a quantity of goods contaminated with at least one organism selected from the group consisting of the genera pseudomonas, escherichia, serratia, klebsiella, proteus, enterobacte, actinetobacter, streptococcus, staphylococcus, aspergillus and candida albicans; and heating the goods in the absence of iodine at a temperature of approximately 117°–150° F. for a time sufficient to sterilize the goods.

2. A method as in claim 1, wherein the time sufficient to sterilize the goods is in the range of 12 hours to 14 days.

3. A method as in claim 2, wherein the temperature is in the range of 122° to 140° F.

4. A method as in claim 2, further comprising the step of identifying any contaminant present in the goods prior to the heating step.

5. A method as in claim 4, wherein the contaminant is identified by performing at least one test selected from the group consisting of a total bacterial count test, a yeast and mold count test, a gram negative bacterial screen test, a gram stain test, an enterobacteriaceae identification test, and a yeast or mold identification test.

6. A method as in claim 1, wherein the goods are housed in a package that comprises a material that will deform when heated to a temperature above 170° F. and below 212° F.

7. A method as in claim 1, wherein the goods comprise at least one emulsion.

8. A method as in claim 1, wherein the goods comprise goods that will separate when heated to a temperature above 170° F.

9. A method as in claim 1, wherein the goods comprise packaged cosmetics.

10. A method for sterilizing goods as in claim 1, wherein the time sufficient to sterilize the goods is greater than 24 hours.

11. A method for sterilizing a packaged product contaminated with at least one organism selected from the group consisting of the genera pseudomonas, escherichia, serratia, klebsiella, proteus, enterobacter, actinetobacter, streptococcus, staphylococcus, aspergillus and candida albicans, the method including the steps of:

providing a packaged product that is contaminated with at least one organism selected from the group consisting of the genera pseudomonas, escherichia, serratia, klebsiella, proteus, enterobacter, actinetobacter, streptococcus, staphylococcus, aspergillus and candida albicans; and heating the packaged product, in the absence of an antibacterial agent, to a temperature in the range of 117°–150° F. for a time sufficient to lower the number of contaminant organisms to less than 10 contaminant organisms per gram of product.

12. A method as in claim 11, further comprising the step of identifying the at least one contaminant organism prior to heating the packaged product.

13. A method as in claim 12, wherein the at least one contaminant organism is identified by performing one or more tests selected from the group consisting of a total bacterial count test, a yeast and mold count test, a gram negative bacterial screen test, a gram stain test, an enterobacteriaceae identification test, and a yeast or mold identification test.

14. A method as in claim 13, wherein the temperature is in the range of 122°–140° F.

15. A method for treating a quantity of goods contaminated with at least one organism, the method comprising the steps of:

(a) providing a quantity of goods contaminated with at least one organism selected from the group consisting of the genera pseudomonas, escherichia, serratia, klebsiella, proteus, enterobacter, actinetobacter, streptococcus staphylococcus, aspergillus and candida albicans and determining the quantity of the at least one contaminant organism in a sample taken from the quantity of goods;

(b) determining whether the at least one organism is a microorganism selected from the group consisting of a bacteria, a yeast, or a mold;

(c) determining a temperature at which the at least one organism can be destroyed within the range of approximately 122°–140° F.

(d) heating the quantity of goods at a temperature in the rage of approximately 122°–140° F. for a time period in the range of 12 hours to 14 days to sterilize the goods; and (e) measuring the level of contaminants remaining in a unit quantity of the goods after heating.

16. A method as in claim 15, wherein the determination of whether the at least one organism is selected from the group consisting of a bacteria, yeast, or mold is carried out by performing at least one test selected from the group consisting of a total bacterial count test, a yeast and mold count test, and a gram negative bacterial screen test.

17. A method as in claim 16, further comprising the step of conducting a gram stain test after performing the at least one test selected from the group consisting of a total bacterial count test, a yeast and mold count test, and a gram negative bacterial screen test: and wherein the at least one test is carried out prior to heating the goods.

18. A method as in claim 17, further comprising the step of conducting a enterobacteriaceae test to determine the identity of bacteria in the at least one contaminant after the gram stain test is completed.

19. A method as in claim 16, further comprising the step of conducting a microscopic wet mount test in order to identify a contaminant selected from the group consisting of a yeast and a mold.

20. A method as in claim 15, wherein the goods comprise at least one emulsion.

* * * * *